United States Patent [19]

Weinstock

[11] 4,437,000
[45] Mar. 13, 1984

[54] APERTURE PIECE AND METHOD FOR CALIBRATING BACKSCATTER THICKNESS MEASURING INSTRUMENTS FOR MEASURING CONCAVE WORKPIECES

[75] Inventor: Jacques Weinstock, Flushing, N.Y.

[73] Assignee: UPA Technology, Inc., Syosset, N.Y.

[21] Appl. No.: 245,936

[22] Filed: Mar. 20, 1981

[51] Int. Cl.³ .................... G01N 23/00; G01D 18/00
[52] U.S. Cl. .................. 250/308; 250/252.1; 250/358.1
[58] Field of Search ............ 250/252.1, 306, 307, 250/308, 359.1, 358.1; 378/89

[56] References Cited

U.S. PATENT DOCUMENTS

| 3,319,067 | 5/1967 | Joffe et al. | 250/308 |
| 3,456,115 | 7/1969 | Lieber et al. | 250/308 |
| 3,714,436 | 1/1973 | Fischer | 250/308 |
| 4,155,009 | 5/1979 | Lieber et al. | 250/252.1 |
| 4,317,997 | 3/1982 | Tiebor et al. | 250/308 |

Primary Examiner—Janice A. Howell
Attorney, Agent, or Firm—Nims, Howes, Collison & Isner

[57] ABSTRACT

An aperture piece to be used in conjunction with backscatter instruments for measuring the thickness of a coating on a substrate of a concave workpiece. The aperture piece being selectively shaped so that a sample support surface, including an aperture through which radiation from a radioisotope is transmitted, may be inserted into the interior space defined by the concave workpiece to engage the concave surface. A method of calibrating backscatter instruments using the aperture piece to make correction for the failure to have a planar mating relation between the sample support surface and the concave workpiece.

2 Claims, 5 Drawing Figures

APERTURE PIECE AND METHOD FOR CALIBRATING BACKSCATTER THICKNESS MEASURING INSTRUMENTS FOR MEASURING CONCAVE WORKPIECES

BACKGROUND OF INVENTION

The present invention relates to an aperture piece to be used in conjunction with backscatter apparatus for non-destructively measuring the thickness of a coating on a substrate.

Backscatter instruments are used to measure thickness of coatings on substrates by irradiating the coating with radiation from a radioactive isotope and counting the particles backscattered from the coatings. The backscatter count provides an indication of the coating thickness. One type of such backscatter instrument is shown and described in U.S. Pat. No. 4,155,009.

In using backscatter instruments, the radiation from the radioactive isotope is directed to the workpiece being measured through an aperture in an aperture piece. The function of the aperture piece is to limit the radiation reaching the workpiece to that radiation permitted to travel through the aperture of the aperture piece thereby ensuring that the same amount of radiation reaches the workpiece from measurement to measurement. A description of a workpiece support and mask (aperture piece) assembly for a backscatter measuring instrument is described in U.S. Pat. No. 3,456,115.

The aperture pieces are conventionally designed with a planar sample support surface for interfacing with the workpiece. In backscatter measurements it is important to have the support surface as flat as possible against the workpiece surface.

With aperture pieces now on the market, workpieces having flat surfaces or surfaces with large radii of curvature are easily measured. As the radii of curvature of the workpiece becomes increasingly smaller more difficulties are encountered in maintaining the planar mating relationship between the sample support surface and the workpiece surface. With convex surfaces conventional aperture pieces may be used to make measurements but the measurements are increasingly inaccurate with smaller radii of curvature because of the difficulty in maintaining or closely approximating the desirable planar mating relationship between the sample support surface and the workpiece surface.

In the electronics industry there has risen a need to measure the thickness of coatings on concave surfaces, for example, the inside surfaces of connectors for receiving connector pins. These surfaces typically have inside diameters in the range of 15 mils to 80 mils. It has been a problem in the industry to measure coating thickness on these interior surfaces. One way to measure these surfaces is to break the hollow connector longitudinally and measure one of the pieces on the concave surface. However, it has long been a problem to measure concave surfaces with these small radii of curvature. The problem results from two difficulties—one, the radii of curvature are so small that the planar mating relationship between the sample support surface of the aperture piece and the workpiece surface has been difficult to obtain, and two, it has been difficult to physically position the sample support surface adjacent to the concave surface because of the interference of the aperture piece with the concave workpiece.

SUMMARY OF INVENTION

The problem of measuring coatings on concave surfaces having small radii of curvature is solved by the present invention.

The aperture piece of the present invention has a base portion having an aperture and a boss portion formed on the base. The boss has a hollow interior and further has an aperture in communication with the hollow interior through which the radiation from the radioactive isotope positioned in the hollow interior is transmitted. The boss is selectively shaped for the particular concave surface to be measured to permit the boss to be inserted within the interior space defined by the concave surface for a measurement of the concave surface. This shaping overcomes the second difficulty noted above.

The backscatter instrument, such as the instrument described in U.S. Pat. No. 4,155,009, which can utilize the aperture piece according to the present invention is first calibrated in the normal manner to calibrate the instrument for the particular substrate-coating combination. In particular, these calibration measurements are made of a sample of substrate material, a sample of coating material and two samples having known coating thickness. All of these samples are flat. In making these calibrations, however, the aperture piece according to the present invention is used. Next, in accordance with the present invention, two additional calibration measurements are made to calibrate the instrument for the particular geometry for the workpiece to be measured. With a workpiece having a concave surface the additional calibration steps overcome the first difficulty noted above. These additional calibration steps are accomplished by making a first measurement of a sample of substrate material, the sample being shaped to have a concave surface having the same inside diameter as the workpiece to be measured, and then making a second measurement of a sample of coating material, this sample shaped to have a concave surface having the same inside diameter as the workpiece to be measured. These two measurements provide the necessary additional information whereby the backscatter instrument can be calibrated following the procedure described in U.S. Pat. No. 4,155,009. After the instrument has been calibrated, accurate and repeatable measurements of the workpiece can then be made.

BRIEF DECRIPTION OF THE DRAWINGS

In order that the invention may be clearly understood and readily carried into effect, a preferred embodiment will now be described, by way of example only, with reference to the accompanying drawings which:

DESCRIPTION OF A PREFERRED EMBODIMENT

Figure 1:
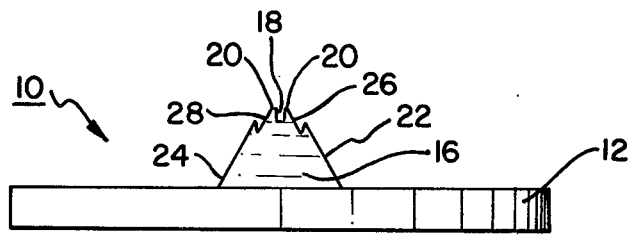
FIG. 1 is an elevational view of the aperture piece according to the present invention.
Figure 2:
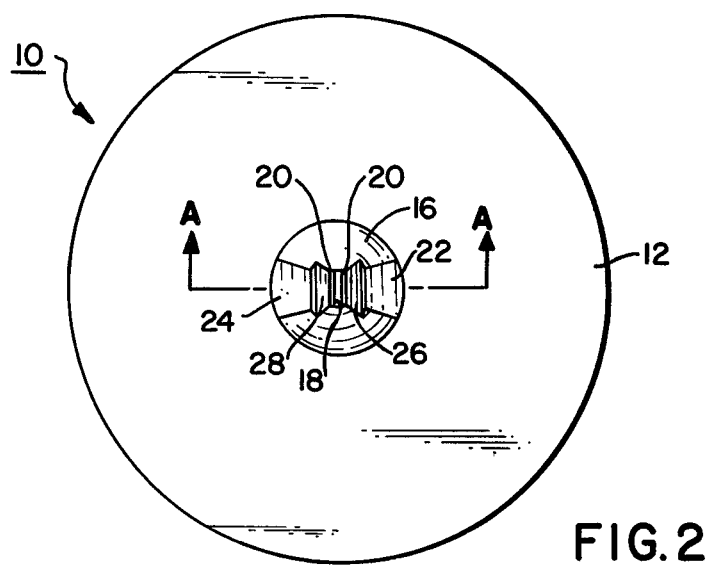
FIG. 2 is a top view of the aperture piece shown in FIG. 1.
Figure 3:
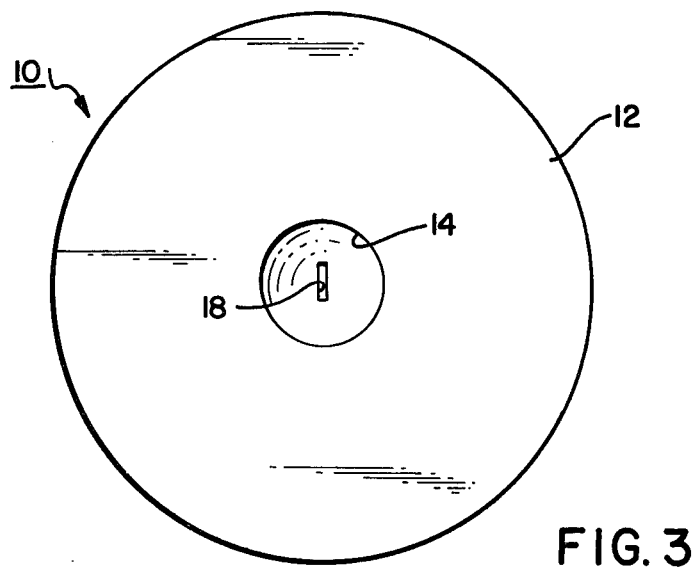
FIG. 3 is a bottom view of the aperture piece shown in FIG. 1.
Figure 5:
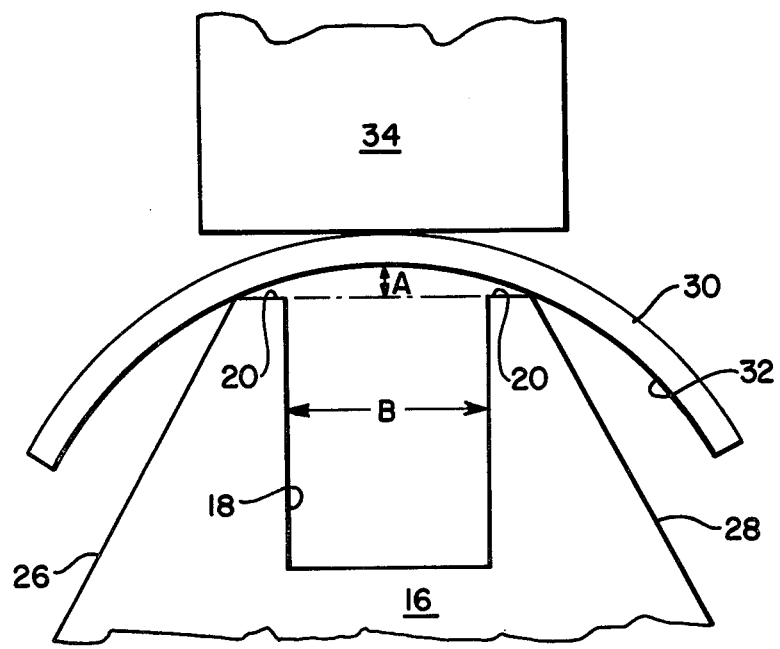
FIG. 5 is a partial schematic view of the aperture piece shown in FIG. 4 in contact with a concave workpiece for a measurement.

An aperture piece 10 is shown in FIGS. 1–3 and partially in FIGS. 5. This aperture piece 10 includes a base 12 having an aperture 14. A boss 16, which in a preferred embodiment has a generally truncated conical shape, is formed on base 12. This boss 16 is generally hollow and has an aperture 18 at the upper surface of the boss 16 to provide passage for radiation from a radioisotope (not shown) which is located within the hollow of the boss 16. The aperture 18 is preferably rectangularly shaped and transmits a preselected amount of radiation from the radioisotope.

Figure 4:
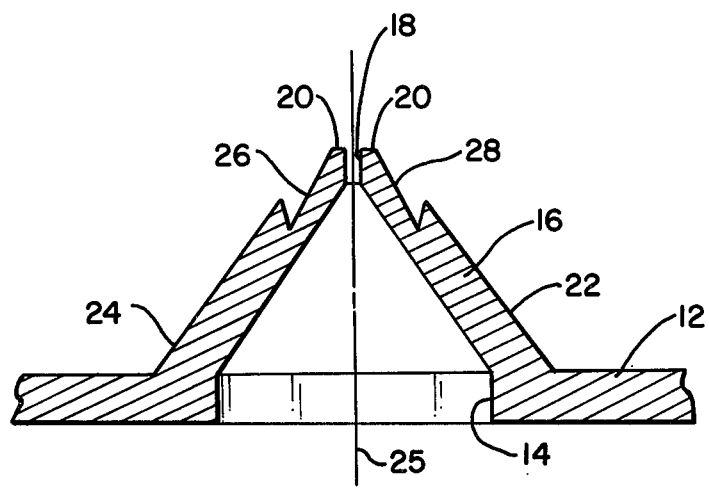
FIG. 4 is a cross-sectional view along A—A in FIG. 2.

The generally conical boss 16 is selectively shaped to provide a planar sample support surface 20 which includes the aperture 18. This surface 20 is narrow in width in comparison with its length measured parallel to the longer edges of aperture 18 thus providing a "knife-edge" surface 20. In a preferred embodiment as shown in FIGS. 1, 2 and 4, the boss 16 is selectively shaped by a pair of first planar cuts 22 and 24 parallel to the longer edges of the rectangular aperture 18, one cut on each side of the aperture. These planar cuts are symmetrical about the axis 25 of the truncated conical boss 16. A pair of second planar cuts 26 and 28 are made adjacent the aperture 18 which again are parallel to the longer edges of rectangular aperture 18, one cut on each side of the aperture 18. These cuts 26 and 28 are symmetrical about the axis 25 of the truncated conical boss 16 and the angle between the pair of second planar cuts 26 and 28 is smaller than the angle between the pair of first planar cuts 22 and 24.

By making cuts 22, 24, and 26, 28, the sample support surface may be inserted into the space defined by a concave workpiece 30 as shown in FIG. 5 without interfering with the side portion of the concave workpiece 30 when the support surface 20 is brought into engagement with the concave surface 32 of workpiece 30. a workpiece holder 34 is provided to hold the workpiece 30 during a measurement.

It is desirable to make the dimension "A" shown in FIG. 5 as small as possible with the dimension "B" large enough to permit sufficient radiation from the radioactive isotope to be transmitted through aperture 18 to provide for proper resolution during the measurement taken.

There will always be some dimension "A" as shown in FIG. 5 when the workpiece to be measured has a concave surface. A correction for the dimension "A" is made when calibrating the backscatter instrument used in making the thickness measurement in accordance with the present invention. For example, with the backscatter instrument described in U.S. Pat. No. 4,155,009, the instrument is calibrated by using the aperture piece 10 according to the present invention in making the normal calibration measurements of a flat sample of substrate alone, a flat sample of the coating material and two flat standards of known coating thickness to enable the instrument to internally compute two constants used to calibrate the instrument for the particular substrate-coating combination.

To properly calibrate this instrument when making measurements of concave surfaces with the aperture piece 10 of the present invention, two additional measurements are made. A first measurement is made of a sample of substrate having a concave surface with the same inside diameter as the workpiece to be measured. A second measurement is made of a sample of coating material also having a concave surface with the same inside diameter as the workpiece to be measured. In the process of calibrating the instrument in this manner, the instrument automatically takes into account a correction factor depending on the dimension "A". This results because the dimension "A" remains the same both during calibration and during the making of an actual thickness measurement.

Once the instrument is thus calibrated measurements of concave surfaces having an inside diameter in the range of 15 mils to 80 mils may be easily made where it has not been possible heretofore.

While the fundamental novel features of the invention have been shown and described, it should be understood that various substitutions, modifications and variations may be made by those skilled in the art without departing from the spirit or scope of the invention. Accordingly, all such modifications and variations are included in the scope of the invention as defined by the following claims:

I claim:

1. An aperture piece for use in conjunction with backscatter type apparatus for measuring the thickness of a thin coating on a concave surface of a workpiece substrate comprising
    a planar base section having a central aperture therein,
    an outwardly extending and progressively tapering hollow boss in the general form of a truncated cone mounted over said central aperture, said hollow boss having a longitudinal axis and outwardly terminating in a small rectangular aperture in the extending end thereof defined by a pair of spaced parallel elongate edges and a pair of spaced parallel short edges disposed perpendicular to said elongate edges,
    said rectangular aperture being of markedly smaller areal extent than said central aperture in said base section,
    the external surface of the base portion of said boss being selectively shaped to include a first pair of diametrically opposed planar converging surfaces disposed parallel to the elongate defining edges of said small rectangular aperture and with the projected included angle between said first pair of surfaces being bisected by the longitudinal axis of said boss,
    the external surface of the upper portion of said boss being further selectively shaped to include a second pair of diametrically opposed planar converging surfaces disposed parallel to the elongate defining edges of said small rectangular aperture and with the projected included angle between said second pair of surfaces being bisected by the longitudinal axis of said boss,
    said second pair of converging surfaces having the upper defining edges thereof disposed in closely adjacent relation with said elongate defining edges of said small rectangular aperture to define a narrow perimetric sample support surface thereabout and defining a projected included angle that is less than the projected included angle between said first pair of converging planar surfaces.
2. In the selective calibration of backscatter apparatus for the measurement of the thickness of a coating on a concave surface of a workpiece substrate of predetermined inside diameter, the steps of selecting an aperture piece having an aperture therein whose marginal defining edges are positionable closely adjacent the concave surface of said workpiece and following standard calibration procedures employing planar standard workpieces, making a first supplemental calibration measurement utilizing the selected aperture piece to obtain a backscatter count for a concave surface of a sample of the substrate material shaped to have the same inside diameter as the workpiece to be measured, and making a second supplemental calibration measurement utilizing the selected aperture piece to obtain a backscatter count for a concave surface of a sample of the coating material shaped to have the same inside diameter as the workpiece to be measured.

whereby subsequent measurements of the thickness of coatings on the concave surfaces of workpieces of said predetermined diameter will be independent of variation of backscatter counts resulting from variation in dimensions of the measurement situs.

* * * * *